United States Patent [19]
Kurz et al.

[11] Patent Number: 6,146,617
[45] Date of Patent: Nov. 14, 2000

[54] DISPERSION OF INORGANIC UV FILTERS

[75] Inventors: Thekla Kurz; Dorothee Wille; Sabine Hitzel, all of Darmstadt, Germany

[73] Assignee: Merck Patent Gesellschaft mit, Germany

[21] Appl. No.: 09/334,070

[22] Filed: Jun. 16, 1999

[30] Foreign Application Priority Data

Jun. 16, 1998 [DE] Germany .................... 198 26 840

[51] Int. Cl.⁷ ............... A61K 7/24; A61K 7/44; A61K 7/00

[52] U.S. Cl. .............. 424/59; 424/60; 424/400; 424/40

[58] Field of Search ............... 424/59, 60, 400, 424/401

[56] References Cited

U.S. PATENT DOCUMENTS

| | | | |
|---|---|---|---|
| 5,296,476 | 3/1994 | Henderson | 514/163 |
| 5,849,909 | 12/1998 | Richard et al. | 424/59 |
| 5,916,544 | 6/1999 | Liu et al. | 424/59 |
| 5,928,630 | 7/1999 | Richard et al. | 424/59 |
| 5,961,961 | 10/1999 | Dobkowski et al. | 424/59 |
| 5,989,528 | 11/1999 | Tanner et al. | 424/59 |

*Primary Examiner*—Shelley A. Dodson
*Attorney, Agent, or Firm*—Millen, White, Zelano & Branigan, P.C.

[57] ABSTRACT

The present invention relates to a dispersion of inorganic UV filters in liquid UV filters and their use in sunscreens.

21 Claims, No Drawings

DISPERSION OF INORGANIC UV FILTERS

SUMMARY OF THE INVENTION

The present invention relates, e.g., to novel dispersions of inorganic UV filters and to the use of these dispersions in sunscreens.

While about 30 years ago sunlight was regarded as therapeutic and safe because of the synthesis of vitamin D, in recent years, opinion in this connection has changed considerably, not only from a medical viewpoint. The potential dangers associated both with natural and artificial irradiation with sunlight have been pushed into the foreground of awareness. In particular, a change in behavior has been brought about as the result of knowledge about the effect of sunlight on skin ageing and the development of skin cancer.

As is known, skin is sensitive to solar rays, which can cause ordinary sunburn or an erythema, also burns of a greater or lesser severity.

Solar rays also have other negative effects; they cause the skin to lose its elasticity and form wrinkles and thus lead to premature ageing. In some cases, dermatoses can also be observed, and in the extreme case, skin cancer can result.

It is also desirable to protect hair against photochemical damage in order to prevent changes in shades, bleaching or damage of a mechanical nature.

As is known, the most hazardous solar rays are those having a wavelength of less than 400 nm. It is also known that, as a result of the presence of the ozone layer in the earth's atmosphere, which absorbs some solar radiation, the lower limit of the ultraviolet rays which reach the earth's surface is about 280 nm.

One aim in the field of sun protection is therefore to ensure good protection against UVB and UVA radiation.

In recent years, inorganic light protection filters have secured a firm place in sun cosmetics.

Suitable inorganic light protection filters which may be mentioned here are titanium dioxide, zinc oxide, iron oxides and cerium oxide.

Micropigments, especially micronized titanium dioxide, are distinguished by their good compatibility and their exceptional stability. Over a broad UV range from 250 to 380 nm, titanium dioxides can be used to achieve extremely effective protection.

The inorganic filters are used in sun protection either as powders or as dispersions in oil or water. Dispersions usually give higher sun protection factors (SPF) since wet grinding (e.g. in a bead mill) can achieve a higher degree of dispersion of the micropigments. However, a disadvantage in this connection is that an auxiliary (the dispersion medium) is already prespecified for the end formulation. This means that during preparation of the corresponding sunscreen, there is no freedom of choice in determining the oil to be used and in most cases the formulations cannot be oil-free.

In addition, the inorganic UV filters used hitherto have dispersion problems since the particles often settle in the cosmetic formulations, meaning that optimum application to the skin is not guaranteed.

An object of the invention was therefore to find a dispersion of inorganic UV filters which ensures free choice of the oil to be used during preparation of the formulations and which solves the dispersion problems just described.

Surprisingly, it has now been found that the dispersion of titanium dioxide, zinc oxide or other inorganic UV filters in a liquid UV filter achieves said objective.

The invention thus provides a dispersion of an inorganic UV filter which is characterized in that the inorganic UV filter is dispersed in a liquid UV filter.

Suitable inorganic UV filters are all pigments which have sunscreening activity. Preference is given to using micronized titanium dioxide, zinc oxide, cerium oxide or iron oxides.

Conventional titanium dioxides have hitherto led to severe whitening of the formulations on the skin.

A particularly preferred embodiment of this invention therefore uses micronized $TiO_2$ as inorganic UV filter. This is commercially available as Eusolex® T-2000 (Merck KGaA, Darmstadt).

Eusolex® T-2000 is a second generation titanium dioxide. This UV filter is a titanium dioxide based on the rutile modification and is in the form of extremely small primary particles. These properties enable high absorption not only in the UVB region, but also in the UVA region. The transparency in the visual spectrum is nevertheless very high. The undesired "whitening" effect does not therefore arise.

Even low concentrations give high sun protection factors. The ratio of UVA to UVB factor is, without further additives, about 0.5:1.

Eusolex® T-2000 can be incorporated easily either into water or into oil or silicone oil. This is to be attributed to a complex modification of the surface, which imparts amphiphilic properties to the product.

In the case of the novel dispersion, a liquid UV filter serves as dispersion medium. This is an extremely practical solution since inorganic UV filters are in any case frequently used in combination with other UV filters.

Preferred liquid UV filters are preferably oil-soluble substances, e.g., from the group consisting of octocrylene (Eusolex® OCR), octyl methoxycinnamate (methoxycinnamic ester, e.g. Eusolex® 2292), homosalicylate (HMS), octyl salicylate (e.g. Eusolex® OS) or octyldimethyl-p-aminobenzoic acid; water-soluble substances, e.g., after neutralization, such as e.g., phenyl-benzimidazole-5-sulfonic acid (Eusolex® 232); or alcohol-soluble substances such as, e.g., 4-amino-benzoic acid (PABA).

A gel former is preferably added to stabilize the dispersion. This may be helpful since, because of the difference in densities between inorganic UV filter pigment and organic UV filter, many inorganic UV filters settle out without the addition of gel formers. The degree of homogeneity of a composition can be determined, e.g., with sedimentation balances or by Andreasen pipettes. The gel former, however, has virtually no effect on the UV filtration properties of the end formulation. Suitable gel formers are typically oil-dispersible builders. Preference is given to using bentones, finely divided silicon dioxide (aerosil) or ethylcellulose in the novel dispersions.

The dispersions are preferably prepared by first preparing a mixture of inorganic UV filter and gel former, into which the liquid UV filter is then incorporated in small portions. It is also possible to first prepare a mixture of liquid UV filter and gel former and then to incorporate the inorganic UV filter into this mixture.

The content of inorganic UV filter in the liquid UV filter (plus optionally, gel former) is about 5 to 80% by weight, preferably about 25 to 50% by weight.

The inorganic UV filter component can either comprise a single inorganic UV filter or a combination of two or more inorganic UV filters. The same is true for the liquid UV filter component.

The content of gel former can strictly speaking be chosen freely, although it is useful to keep this content as low as possible. The content is preferably up to about 10% by weight, and is particularly preferably about 5% by weight.

The novel dispersions make it possible for the formulator to use oils of his choosing or even to prepare formulations which are oil-free. High sun protection factors (SPFs) can be achieved without incurring dispersion problems with the inorganic pigments.

According to the invention, dispersions comprising these UV filters can be used separately or, of course, also in combination with other organic or inorganic UVA and UVB filters or their mixtures in sunscreens.

The invention thus also provides for the use of a novel dispersion in cosmetic formulations such as sunscreens, skin creams or gels, hair gels or cosmetic sticks.

The invention also provides sunscreens which comprise a novel dispersion of inorganic UV filters in a liquid UV filter.

The novel dispersion can be incorporated into cosmetic formulations in a concentration of about 0.5 to 30% by weight, preferably about 5 to 20% by weight. In this way, it is possible to prepare formulations in which up to about 100% of the light protection filters used are present in the novel dispersion. The novel dispersions can easily be dissolved, dispersed or emulsified with water and oil.

The novel dispersions can be incorporated directly into cosmetic formulations without further preparatory measures.

These dispersions additionally offer the great advantage of showing no toxic or allergic reactions towards the skin.

The novel cosmetic formulations exhibit clearly improved protection against the harmful effects of solar rays. Furthermore, dispersion problems, which have hitherto played a large role in formulations comprising inorganic UV filters, can be lessened.

A method of protecting skin against solar rays, which involves applying a novel cosmetic preparation to the skin, is likewise provided by the invention.

A combination of the novel dispersion with further organic or inorganic UV filters is possible and also preferable.

Suitable organic UV filters are all UVA and also UVB filters known to the person skilled in the art. For both UV regions, there are many substances which have proven successful and are known from the specialist literature. Examples which may be listed here include benzylidenecampher compounds (e.g. Eusolex® 6300) or phenylbenzimidazole-5-sulfonic acid (Eusolex® 232), benzoyl or dibenzoylmethane such as Eusolex® 9020 or Eusolex® 8020, benzophenones (Eusolex® 4360), methoxycinnamic esters (e.g. Eusolex® 2292), salicylate compounds (e.g. Eusolex® OS), octocrylene (Eusolex® OCR), 4-aminobenzoic acid (PABA), homosalicylate (HMS) or octyl triazones (Uvinul® T 150).

These organic UV filters are typically incorporated into cosmetic formulations in an amount of about 0.5 to 10% by weight, preferably about 1 to 8%.

Suitable inorganic UV filters are UV filters generally known to the person skilled in the art, such as, for example, those from the group consisting of titanium dioxide and zinc oxide. These inorganic UV filters are usually incorporated into cosmetic formulations in an amount of about 0.5 to 20% by weight, preferably about 2 to 10%.

The novel dispersions have high chemical stability, i.e. are not hydrolyzable, photooxidizable or oxidizable, have high thermal stability and good perspiration-resistance.

If desired, the novel sunscreens may also comprise one or more chemical substances having self-tanning properties.

The chemical substances having self-tanning properties employed may be any natural and synthetic substances known to the person skilled in the art which are suitable for the preparation of cosmetic formulations. These may be vegetable extracts or synthetic self-tanning agents, such as, for example, dihydroxyacetone or a-ketols.

Furthermore, the novel formulations can also be used for the preventive treatment of inflammation and allergies of the skin and also in certain cases for preventing certain types of cancer.

The novel preparation is used as an agent for protecting the human epidermis or hair or else sensitized hair or as a sunscreen. "Sensitized hair" is taken to mean hair which has been subjected to a permanent wave treatment, or to a coloring or bleaching process.

The novel cosmetic preparation can be used for protecting the human epidermis from solar irradiation. For this purpose, it can be in a variety of forms customarily used for this product type. Therefore, it can, in particular, be in the form of a lotion or emulsion, such as a cream or milk (O/W, W/O), or in the form of oily or oily-alcoholic lotions, emulsions, such as creams or as milk, in the form of oily-alcoholic, oily-aqueous or aqueous-alcoholic gels or as solid sticks, or can be formulated as an aerosol.

The formulation can comprise cosmetic adjuvants which are customarily used in this type of preparation, such as, for example, thickeners, emollients, moisturizers, surface-active agents, emulsifiers, preservatives, antifoams, perfumes, waxes, lanolin, propellants, dyes and/or pigments which color the agent itself or the skin, and other ingredients customarily used in cosmetics.

The gel former (dispersion auxiliary) or solubilizing agent can be an oil, wax or other fatty substances, a lower monoalcohol or a lower polyol or mixtures thereof. Particularly preferred monoalcohols or polyols include ethanol, isopropanol, propylene glycol, glyceryl and sorbitol.

A preferred embodiment of the invention is an emulsion which is in the form of a protective cream or milk and, apart from the novel dispersion (comprising an inorganic UV filter in a liquid UV filter) and optionally further light protection filters, comprises fatty alcohols, fatty acids, fatty acid esters, in particular triglycerides of fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol and oils, waxes and fatty acid esters, such as triglycerides of fatty acids.

The novel cosmetic preparation can also be in the form of an alcoholic gel which comprises one or more lower alcohols or lower polyols such as ethanol, propylene glycol or glycerol, and a thickener, such as silica. The oily-alcoholic gels further comprise natural or synthetic oil or wax.

The solid sticks comprise natural or synthetic waxes and oils, fatty alcohols, fatty acids, fatty acid esters, lanolin and/or other fatty substances.

If a preparation is formulated as an aerosol, use is usually made of customary propellants, such as alkanes, fluoroalkanes and chlorofluoroalkanes.

If the novel composition is to protect natural or sensitized hair from solar irradiation, it can be in the form of a shampoo, lotion, gel or emulsion for rinsing out, in which case the respective formulation is applied before or after shampooing, before or after coloring or bleaching, or before or after permanent waving; or the composition can be in the form of a lotion or gel for styling and treating, a lotion or gel for brushing or setting a water wave, as hairspray, permanent waving composition, colorant or bleach for the hair. As well as comprising the novel dispersions (comprising an inorganic UV filter in a liquid UV filter) and optionally further light protection filters, this composition can also comprise a variety of adjuvants used in this type of composition, such as surface-active agents, thickeners, polymers, emollients, preservatives, foam stabilisers, electrolytes, organic solvents, silicone derivatives, oils, waxes, degreasing agents, dyes and/or pigments which color the composition itself or the hair, or other ingredients customarily used for hair care.

The novel cosmetic preparations can be prepared using techniques which are well known to a person skilled in the art.

In the foregoing and in the following examples, all temperatures are set forth uncorrected in degrees Celsius; and, unless otherwise indicated, all parts and percentages are by weight.

The entire disclosure of all applications, patents and publications, cited above and below, and of German application No. 198 26 840.8 filed Jun. 16, 1998 is hereby incorporated by reference.

The examples below serve to illustrate the invention in more detail.

EXAMPLES

Example 1

The components below are used to prepare a novel sunscreen cream (W/O) containing a UV filter suspension.

|   |                                    |     | % by weight |
|---|------------------------------------|-----|-------------|
| A | UV Filter suspension (see C)       |     | 15.00       |
|   | Eusolex ® 9020 (Art. No. 105844)   | (1) | 2.00        |
|   | Abil EM 90                         | (2) | 3.00        |
|   | Jojoba oil                         | (3) | 5.00        |
|   | Cetiol V                           | (4) | 1.00        |
|   | Prisorine 2021                     | (5) | 4.00        |
|   | Castor oil                         | (6) | 1.00        |
|   | Lunacera W 80                      | (7) | 1.50        |
|   | Oxynex K liquid (Art. No. 108324)  | (1) | 0.05        |
| B | Glycerol (Art. No. 104093)         | (1) | 2.00        |
|   | Sodium chloride (Art. No. 106400)  | (1) | 0.40        |
|   | Preservative                       |     | q.s.        |
|   | Water, demin.                      |     | ad 100.00   |

Possible preservatives are 0.05% propyl 4-hydroxybenzoate (Art. No. 107427) or 0.15% methyl 4-hydroxybenzoate (Art. No. 106757).

C UV Filter Suspension

| Eusolex ® T-2000 (Art No. 105373) | (1) | 30.00% |
|-----------------------------------|-----|--------|
| Eusolex ® OCR (Art. No. 105377)   | (1) | 65.00% |
| Aerosil R 812                     | (8) | 5.00%  |

Firstly, Eusolex® T-2000 is mixed with the aerosil, and then the Eusolex® OCR is added. The mixture is stirred until it is homogeneous.

Preparation:

The components of phase A are mixed and heated to 75° C. The premixed phase B is incorporated into this phase with stirring. The mixture is stirred until it is homogeneous and left to cool with stirring.

Sources of supply:

(1) Merck KGaA, Darmstadt (2) Th. Goldschmidt, Essen (3) Lamotte, Bremen (4) Henkel KGaA, Düsseldorf (5) Unichema, Emmerich (6) Heess, Stuttgart (7) Fuller, Lüneburg (8) Degussa, Frankfurt.

Example 2

The components below are used to prepare a novel sunscreen cream (W/O) containing a UV filter suspension.

|   |                                    |     | % by weight |
|---|------------------------------------|-----|-------------|
| A | UV Filter suspension (see C)       |     | 15.00       |
|   | Eusolex ® 9020 (Art. No. 105844)   | (1) | 2.00        |
|   | Abil EM 90                         | (2) | 3.00        |
|   | Jojoba oil                         | (3) | 5.00        |
|   | Cetiol V                           | (4) | 1.00        |
|   | Prisorine 2021                     | (5) | 4.00        |
|   | Castor oil                         | (6) | 1.00        |
|   | Lunacera W 80                      | (7) | 1.50        |
|   | Oxynex K liquid (Art. No. 108324)  | (1) | 0.05        |
| B | Glycerol (Art. No. 104093)         | (1) | 2.00        |
|   | Sodium chloride (Art. No. 106400)  | (1) | 0.40        |
|   | Preservative                       |     | q.s.        |
|   | Water, demin.                      |     | ad 100.00   |

Possible preservatives are 0.05% propyl 4-hydroxybenzoate (Art. No. 107427) or 0.15% methyl 4-hydroxybenzoate (Art. No. 106757).

C UV Filter Suspension

| Eusolex ® T-2000 (Art No. 105373) | (1) | 30.00% |
|-----------------------------------|-----|--------|
| Eusolex ® OCR (Art. No. 105377)   | (1) | 65.00% |
| Bentone Paste SIL                 | (8) | 5.00%  |

The bentone paste and Eusolex® OCR are mixed in order to disperse the paste. Eusolex® T-2000 is then added thereto successively and stirring is continued until the suspension becomes homogeneous.

Preparation:

The components for Phase A are mixed and heated to 75° C. Phase B, which has been premixed and heated to 80° C, is incorporated into this phase with stirring. The mixture is stirred until it is homogeneous and left to cool with stirring.

Sources of supply:

(1) Merck KGaA, Darmstadt (2) Th. Goldschmidt, Essen (3) Lamotte, Bremen (4) Henkel KGaA, Düsseldorf (5) Unichema, Emmerich (6) Heess, Stuttgart (7) Fuller, Lüneburg (8) Kronos Titan, Leverkusen.

Example 3

The components below are used to prepare a novel sunscreen cream (W/O) containing a UV filter suspension.

|   |                                      |     | % by weight |
|---|--------------------------------------|-----|-------------|
| A | UV Filter suspension (see C)         |     | 10.00       |
|   | Eusolex ® 6300 (Art. No. 105385)     | (1) | 3.00        |
|   | Dow Corning 3225 C                   | (2) | 12.00       |
|   | Dow Corning 344                      | (2) | 2.50        |
|   | Solvent ID                           | (3) | 7.30        |
|   | Bentone paste SIL                    | (6) | 14.50       |
|   | Witconol 14                          | (4) | 2.50        |
|   | Beeswax, white (Art. No. 111544)     | (1) | 2.00        |
|   | Carnauba wax                         | (5) | 0.50        |
| B | 1,2-propanediol (Art. No. 107478)    | (1) | 2.00        |
|   | Sodium chloride (Art. No. 106400)    | (1) | 2.00        |
|   | Preservative                         |     | q.s.        |
|   | Water, demin.                        |     | ad 100.00   |

A suitable preservative is 0.20% Euxyl K 400 (Schülke & Mayr, Norderstedt).

C UV Filter Suspension

| Eusolex ® T-2000 (Art No. 105373) | (1) | 25.00% |
|-----------------------------------|-----|--------|
| Eusolex ® 2292 (Art. No. 105382)  | (1) | 70.00% |
| Bentone Paste SIL                 | (6) | 5.00%  |

The bentone paste and the Eusolex 2292 are mixed in order to disperse the paste. Eusolex T-2000 is then added thereto successively and stirring is continued until the suspension is homogeneous.

Preparation:

Phases A and B are each mixed and heated to 80° C. Phase B is then introduced into phase A. The mixture is stirred until it is homogeneous and left to cool with stirring.

Sources of supply:
(1) Merck KGaA, Darmstadt
(2) Dow Corning, Düsseldorf
(3) BP, Dusseldorf
(4) Witco Chemical, Frankfurt
(5) Aug. Schmidt Nachfolger, Bremen
(6) Kronos Titan, Leverkusen The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A composition comprising a dispersion of an inorganic UV filter, which is a micronized metal oxide, in a liquid UV filter and, as a dispersion auxiliary, bentone, aerosil and/or ethylcellulose.

2. The composition according to claim 1, wherein said inorganic UV filter is micronized titanium dioxide, zinc oxide, cerium oxide or iron oxide.

3. The composition according to claim 2, wherein said inorganic UV filter is micronized titanium dioxide.

4. The composition according to claim 1, wherein said liquid UV filter is octocrylene, octyl methoxycinnamate, homosalicylate, octylsalicylate or octyldimethyl-p-aminobenzoic acid.

5. The composition according to claim 1, wherein said dispersion auxiliary is 5% by weight.

6. The composition according to claim 1, wherein the content of inorganic UV filter is 5 to 80% by weight.

7. The composition according to claim 6, wherein the content of inorganic UV filter is 25–50% by weight.

8. The composition according to claim 1, wherein said inorganic UV filter is micronized titanium dioxide (30% by weight), said liquid UV filter is octocrylene (65% by weight), and said dispersion auxiliary is aerosil (5% by weight).

9. The composition according to claim 1, wherein said inorganic UV filter is micronized $TiO_2$ (30% by weight), said liquid UV filter is octocrylene (65% by weight), and said gel former is a bentone (5% by weight).

10. The composition according to claim 1, wherein said inorganic UV filter is micronized $TiO_2$ (25% by weight), said liquid UV filter is octyl methoxycinnamate (70% by weight), and said gel former is a bentone (5% by weight).

11. A method of making the composition of claim 1, comprising
  a) mixing said inorganic UV filter with said dispersion auxiliary, and
  b) incorporating said liquid UV filter into mixture a) in small portions.

12. A method of making the composition of claim 1, comprising
  a) mixing said liquid UV filter with said dispersion auxiliary, and
  b) incorporating said inorganic UV filter into mixture a).

13. In a sunscreen, skin cream or gel, hair gel or cosmetic stick composition comprising a UV filter and a sunscreen, skin cream or gel, hair gel or cosmetic formulation base, the improvement wherein the UV filter is a composition according to claim 1.

14. A sunscreen, skin cream or gel, hair gel or cosmetic composition according to claim 13, prepared by a process wherein a dispersion of the inorganic filter in a liquid UV filter is combined with said sunscreen, skin cream or gel, hair gel or cosmetic composition.

15. A composition according to claim 13, which is oil-free.

16. A combination comprising a composition according to claim 1 and an organic or inorganic UVA and/or UVB filter.

17. The composition according to claim 16, wherein said UVA and/or UVB filter is a benzylidenecampher compound, phenylbenzimidazole-5-sulfonic acid, benzoyl or dibenzoylmethane, benzophenone, methoxycinnamic ester, salicylate compound, octocrylene, 4-amino-benzoic acid, homosalicylate or octyltriazone.

18. A sunscreen which comprises a composition according to claim 1.

19. A composition according to claim 1, which is oil-free.

20. The composition according to claim 3, wherein said inorganic filter is Eusolex®T-2000.

21. The composition according to claim 1, wherein the particle size of said micronized metal oxide is less than 0.1 micron.

* * * * *